US009517007B2

(12) United States Patent
Uchida (10) Patent No.: US 9,517,007 B2
(45) Date of Patent: Dec. 13, 2016

(54) IMAGE PROCESSING APPARATUS, IMAGE PROCESSING METHOD, AND STORAGE MEDIUM (71) Applicant: CANON KABUSHIKI KAISHA, Tokyo (JP)

(72) Inventor: Hiroki Uchida, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 99 days.

(21) Appl. No.: 14/451,921

(22) Filed: Aug. 5, 2014

(65) Prior Publication Data
US 2015/0042952 A1 Feb. 12, 2015

(30) Foreign Application Priority Data

Aug. 7, 2013 (JP) ................. 2013-164230

(51) Int. Cl.
A61B 3/14 (2006.01)
A61B 3/00 (2006.01)
A61B 3/10 (2006.01)
G06T 7/00 (2006.01)
G06T 11/00 (2006.01)

(52) U.S. Cl.
CPC ............. *A61B 3/102* (2013.01); *G06T 7/0081* (2013.01); *G06T 11/003* (2013.01); *G06T 2207/10101* (2013.01); *G06T 2207/30041* (2013.01)

(58) Field of Classification Search
USPC ................................. 351/206, 246
See application file for complete search history.

(56) References Cited

U.S. PATENT DOCUMENTS

2006/0119858 A1   6/2006   Knighton

FOREIGN PATENT DOCUMENTS

JP   2012-161595 A   8/2012

Primary Examiner — Jack Dinh
(74) Attorney, Agent, or Firm — Canon USA, Inc. I.P. Division (57) ABSTRACT An ophthalmic apparatus determines, based on information indicating a tilt of an object in a tomographic image, a direction in which luminance information of the tomographic image is to be combined. Then, the ophthalmic apparatus combines the luminance information of the tomographic image along the determined direction, thereby generating a plane image of the object.

29 Claims, 11 Drawing Sheets

IMAGE PROCESSING APPARATUS, IMAGE PROCESSING METHOD, AND STORAGE MEDIUM

BACKGROUND OF THE INVENTION

1. Field of the Invention

The present invention relates to a technique for generating plane image data of an object.

2. Description of the Related Art

Application of an optical coherence tomographic imaging apparatus using optical coherence tomography (OCT) utilizing multi-wavelength lightwave interference to the human body has been increasing to acquire information about, for example, internal organs and retina.

The optical coherence tomographic imaging apparatus irradiates a sample with measurement light, which is low coherent light, and then uses an interference system to enable measurement of back-scattered light from the sample. When the optical coherence tomographic imaging apparatus is applied to the eyes, the optical coherence tomographic imaging apparatus scans a subject's eye with the measurement light to enable high-resolution imaging of tomographic image data of the subject's eye. Thus, the optical coherence tomographic imaging apparatus is widely used in ophthalmic diagnosis of the retina, etc.

The optical coherence tomographic imaging apparatus irradiates a point on the fundus with the measurement light so that information (A-scan information) about the point on the fundus along the depth direction can be obtained. The optical coherence tomographic imaging apparatus acquires a plurality of pieces of A-scan information by scanning with the measurement light, whereby tomographic image data (B-scan information) of the retina along the depth direction can be acquired.

The optical coherence tomographic imaging apparatus can also acquire a plurality of pieces of B-scan information by shifting the scanning position. For example, the optical coherence tomographic imaging apparatus acquires B-scan information several hundreds of times in the horizontal direction while shifting the scanning position in the longitudinal direction, thereby acquiring three-dimensional tomographic image data of the retina including a plurality of sets of tomographic image data. The plurality of sets of tomographic image data thus acquired contains information about the entire retina along the depth direction and, thus can provide information that is significantly helpful for the diagnosis of retinal disease.

U.S. Patent Application Publication No. 2006/119858 discusses a technique for reconstructing pseudo fundus plane image data (intensity image data) from a plurality of sets of tomographic image data. Specifically, the technique combines a plurality of pieces of information along the depth direction obtained from a single piece of A-scan information into a single piece of information and acquires the combined information for every A-scan information, whereby intensity image data of the retina can be generated only from tomographic image data.

SUMMARY OF THE INVENTION

According to an aspect of the present invention, an image processing apparatus includes an acquisition unit configured to acquire a tomographic image of an object, a determination unit configured to determine a direction based on information indicating a tilt of the object in the tomographic image, and a generation unit configured to generate a plane image of the object by combining luminance information of the tomographic image along the determined direction.

Further features of the present invention will become apparent from the following description of exemplary embodiments with reference to the attached drawings.

DESCRIPTION OF THE EMBODIMENTS

The conventional technique combines pieces of information together in the direction (A-scan direction) perpendicular to tomographic image data to generate intensity image data. This causes a problem that the size of the retina formed on the intensity image data changes according to the tilt of the retina on the tomographic image data. Since a doctor observes a retinal structure or the size of a lesion in the intensity image data, a change in the structure or the size of a lesion according to the tilt of the retina in the tomographic image data can mislead the doctor in his/her diagnosis.

In view of the foregoing, the present exemplary embodiment is directed to generating appropriate plane image data of an object regardless of the tilt of the object in tomographic image data.

In the present exemplary embodiment, the direction in which pieces of luminance information of tomographic image data are to be combined together is determined based on information indicating the tilt of an object in the tomographic image data of the object, and the pieces of luminance information of the tomographic image data are combined together along the determined direction.

Thereby, appropriate plane image data of the object can be generated regardless of the tilt of the object in the tomographic image data.

Various exemplary embodiments, features, and aspects of the invention will be described in detail below with reference to the drawings. The object to be measured in the present exemplary embodiment may be any object other than the subject's eye, such as internal organs and skin of a subject. Further, the apparatus according to the present exemplary embodiment may be any apparatus other than the ophthalmic apparatus, such as an optical coherence tomographic imaging apparatus and an image processing apparatus (for example, a computer 1003) configured to process tomographic images.

(Configuration of Ophthalmic Apparatus)

Figure 1A:
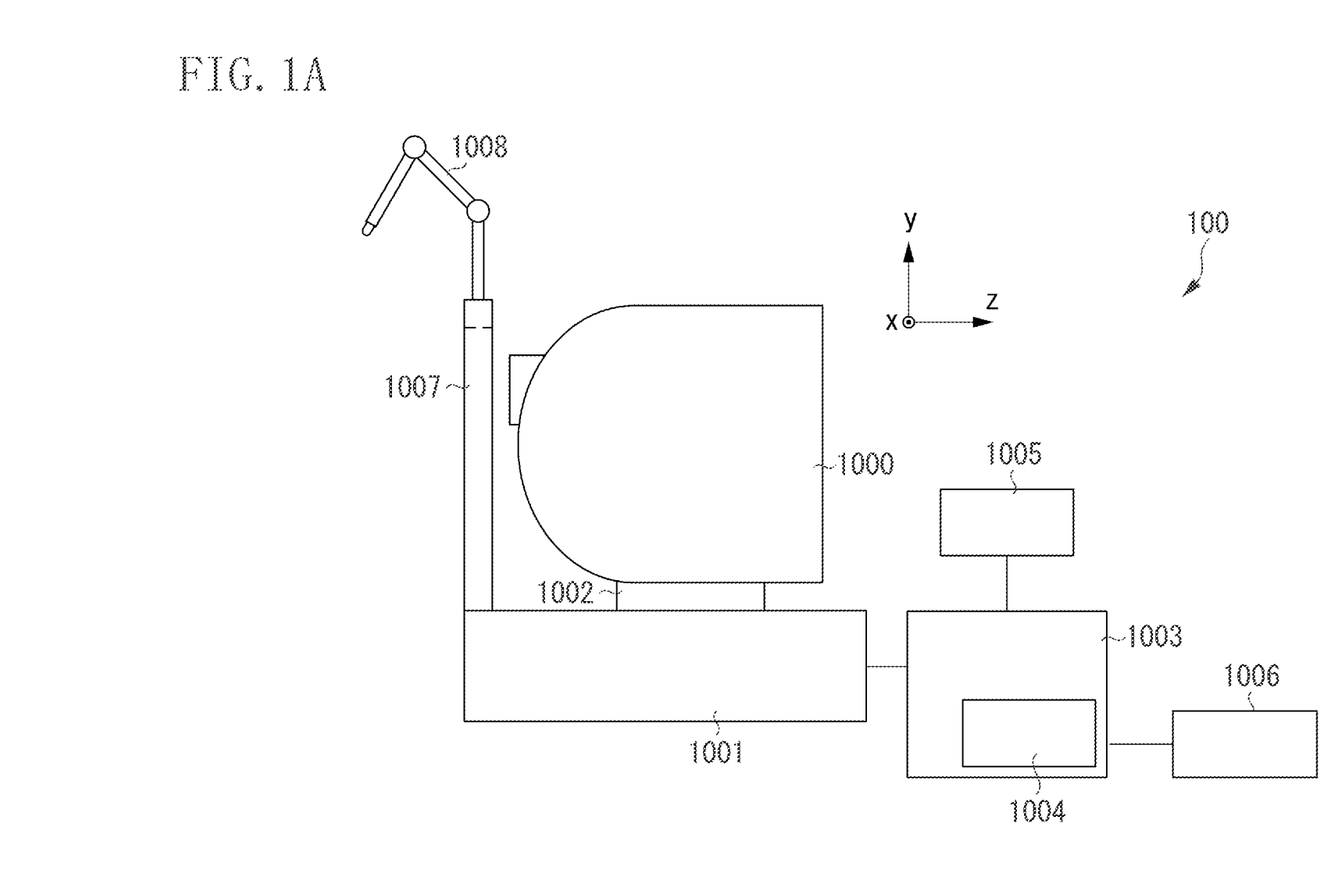
FIGS. 1A and 1B each illustrate the configuration of an ophthalmic apparatus according to an exemplary embodiment of the present invention.
Figure 1B:
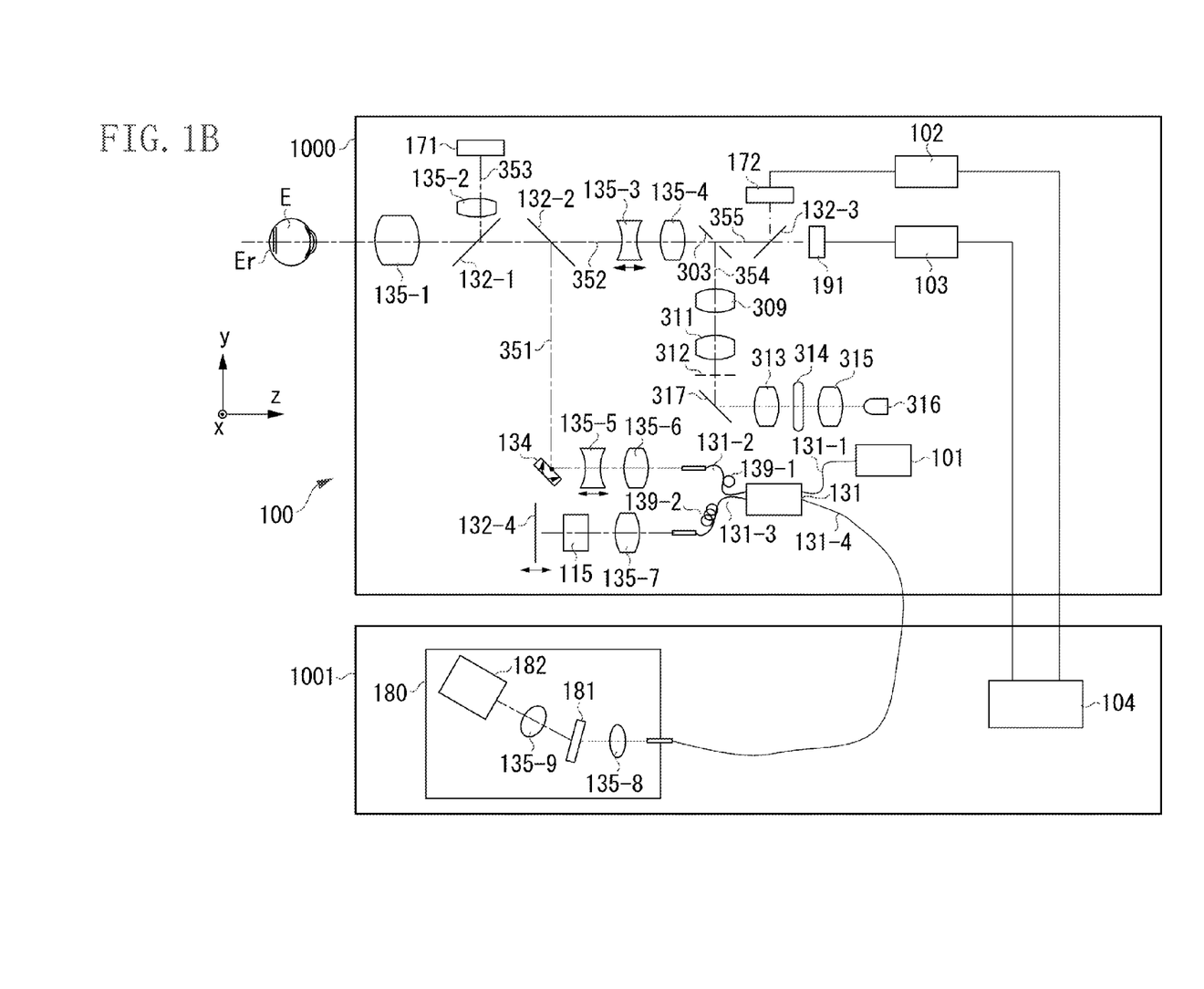

The following describes the first exemplary embodiment of the present invention. FIGS. 1A and 1B each illustrate the configuration of an ophthalmic apparatus according to the first exemplary embodiment of the present invention. Specifically, FIG. 1A illustrates the external configuration of the ophthalmic apparatus according to the present exemplary embodiment, and FIG. 1B illustrates the internal configurations of an optical head and a base unit of the ophthalmic apparatus according to the present exemplary embodiment. The ophthalmic apparatus is an example of an image processing system.

FIG. 1A illustrates an ophthalmic apparatus 100. An optical head 1000 is an optical measurement system for imaging anterior eye surface image data showing the surface of an anterior eye portion, fundus plane image data showing the surface of a fundus, and fundus tomographic image data showing the cross section of the fundus. A stage unit 1002 moves the optical head 1000 in x-y-z directions specified in FIG. 1A by use of a motor (not illustrated). A base unit 1001 includes a spectrometer to be described below.

The computer 1003 controls processing by which the stage unit 1002 moves the optical head 1000. The computer 1003 also controls imaging processing of fundus tomographic image data. A hard disk 1004 is included in the computer 1003 and stores information about a subject, and programs for imaging fundus tomographic image data, for example. A monitor 1005 is a display unit. An examiner uses an input unit 1006 to give a command to the computer 1003. Specifically, the input unit 1006 includes a keyboard and a mouse. A jaw rest 1007 fixes the jaw and forehead of a subject to facilitate fixing of the eyes of the subject (subject's eye). An external fixation lamp 1008 is used for the fixation of the subject's eye.

The following describes the internal configurations of the optical head 1000 and the base unit 1001, with reference to FIG. 1B. First, the internal configuration of the optical head 1000 will be described. An objective lens 135-1 is disposed to face a subject's eye E. First and second dichroic mirrors 132-1 and 132-2 on an optical axis of the objective lens 135-1 divide the optical path by wavelength band into an optical path 351 of an OCT optical system, an optical path 352 for fundus observation and for a fixation lamp, and an optical path 353 for the observation of the anterior eye portion. Lenses 135-3 and 135-4 are provided, and the lens 135-3 is driven by a motor (not illustrated) to adjust the focus of a fixation lamp 191 and a fundus observation charge-coupled device (CCD) 172.

A perforated mirror 303 is disposed between the lens 135-4 and a third dichroic mirror 132-3 to divide the optical path 352 into optical paths 355 and 354. The optical path 354 forms an illumination optical system configured to illuminate the fundus of the subject's eye E. On the optical path 354, a light emitting diode (LED) light source 316 and a stroboscopic tube 314 are disposed. The LED light source 316 is a fundus observation illumination light source used for positioning of the subject's eye E. The stroboscopic tube 314 is used for imaging of fundus image data of the subject's eye E. Condenser lenses 313 and 315 and a mirror 317 are disposed. Illumination light from the LED light source 316 and the stroboscopic tube 314 is formed into a ring-shaped light flux by a ring slit 312 and reflected by the perforated mirror 303 to illuminate a retina Er of the subject's eye E. Lenses 309 and 311 are provided. The LED light source 316 has a center wavelength at about 780 nm. The retina Er is an example of an object.

The optical path 355 after the perforated mirror 303 is divided by the third dichroic mirror 132-3 by wavelength band into an optical path toward the fundus observation CCD 172 and an optical path toward the fixation lamp 191. The fundus observation CCD 172 has sensitivity at about the center wavelength (780 nm) of the LED light source 316, which is the fundus observation illumination light source. The fundus observation CCD 172 is connected to a CCD control unit 102. The fixation lamp 191 generates visible light to facilitate fixation of a subject' eye. The fixation lamp 191 is connected to a fixation lamp control unit 103.

The CCD control unit 102 and the fixation lamp control unit 103 are connected to a calculation unit 104. The base unit 1001 and the computer 1003 send or receive data to or from each other via the calculation unit 104. On the optical path 353, a lens 135-2 and an anterior eye observation CCD 171 are disposed. The anterior eye observation CCD 171 has sensitivity at about the wavelength (970 nm) of anterior eye observation illumination light (not illustrated). On the optical path 353, an image splitting prism (not illustrated) is also disposed so that the distance of the optical head 1000 in the z-direction with respect to the subject's eye E can be detected as a split image in an anterior eye observation image.

The optical path 351 forms the OCT optical system for imaging of fundus tomographic image data of the fundus Er of the subject's eye E. More specifically, the optical path 351 is used for obtaining interference signals for generating fundus tomographic image data. An X-Y scanner 134 is used for scanning the fundus with light. The X-Y scanner 134 is illustrated as a single mirror but is configured to scan in X-Y two axial directions. Among lenses 135-5 and 135-6, the lens 135-5 is driven by a motor (not illustrated) to adjust the focus of light from a light source 101 emitted from a fiber 131-2 connected to an optical coupler 131 onto the fundus Er. This focus adjustment causes an image of the light from the fundus Er to be simultaneously formed in the shape of a spot onto a leading end of the fiber 131-2.

The following describes the configuration of the optical path from the light source 101, reference optical system, and spectrometer. FIG. 1B illustrates the light source 101, a mirror 132-4, a dispersion compensation glass 115, the optical coupler 131, single-mode optical fibers 131-1 to 131-4 connected to the optical coupler 131 and integrated, a lens 135-7, and a spectrometer 180.

The foregoing configuration forms a Michelson interference system. Light emitted from the light source 101 passes through the optical fiber 131-1 and is split via the optical coupler 131 into measurement light of the optical fiber 131-2 and reference light of an optical fiber 131-3. The measurement light passes through the optical path of the OCT optical system described above, illuminates the fundus Er of the subject's eye E, which is an observation target, and is reflected or scattered by the retina to reach the optical coupler 131 via the same optical path.

On the other hand, the reference light passes through the optical fiber 131-3, the lens 135-7, and the dispersion compensation glass 115, reaches the mirror 132-4, and is reflected. The dispersion compensation glass 115 is inserted to align the dispersion of the measurement light with the dispersion of the reference light. Then, the reflected light returns the same optical path to reach the optical coupler 131.

The optical coupler 131 combines the measurement light and the reference light together to form interference light. Interference occurs when the optical path lengths of the measurement light and the reference light become substantially the same. The mirror 132-4 is held in such a way that the mirror 132-4 can be adjusted in the optical axis direction by a motor (not illustrated) and a driving mechanism (not illustrated), and the optical path length of the reference light can be adjusted to the optical path length of the measurement light, which changes according to the subject's eye E. The interference light is guided to the spectrometer 180 via the optical fiber 131-4.

A polarization adjustment unit 139-1 for the measurement light is provided in the optical fiber 131-2. A polarization adjustment unit 139-2 for the reference light is provided in the optical fiber 131-3. The polarization adjustment units 139-1 and 139-2 include several portions formed by routing the respective optical fibers in a loop shape. The loop-shaped portions are rotated about the longitudinal direction of the respective fibers to apply torsion to the fibers, whereby each of the polarization states of the measurement light and the reference light can be adjusted to each other. In the present exemplary embodiment, the polarization states of the measurement light and the reference light are adjusted and fixed in advance.

The spectrometer 180 includes lenses 135-8 and 135-9, a grating 181, and a line sensor 182. The interference light emitted from the optical fiber 131-4 passes through the lens 135-8 to become substantially parallel light. Then, the substantially parallel light is dispersed by the grating 181 and then an image of the light is formed onto the line sensor 182 by the lens 135-9.

The following describes the light source 101. The light source 101 is a super luminescent diode (SLD), which is a typical low coherent light source. The center wavelength is 855 nm, and the wavelength band width is about 100 nm. Here, the band width is an important parameter because it affects the resolution of an acquired tomographic image in the optical axis direction. As to the type of the light source, while the SLD is selected in the present exemplary embodiment, any light source capable of emitting low coherent light can be used. Thus, amplified spontaneous emission (ASE) and the like can also be used. Considering that the object to be measured is an eye, the center wavelength is desirably near-infrared light. It is also desirable that the center wavelength be as short as possible because the center wavelength affects the resolution of an acquired tomographic image in the horizontal direction. For the foregoing reasons, the center wavelength is set to 855 nm.

While the present exemplary embodiment employs the Michelson interferometer as the interferometer, a Mach-Zehnder interferometer may also be used. Desirably, a Mach-Zehnder interferometer is used if the difference between the amount of measurement light and the amount of reference light is large, or a Michelson interferometer is used if the difference is relatively small.

The following describes imaging processing of the subject's eye E which is executed by the ophthalmic apparatus 100 according to the present exemplary embodiment. First, an examiner lets a patient sit down in front of the ophthalmic apparatus 100 and then starts capturing fundus plane image data showing a surface of the fundus Er of the subject's eye E. Light emitted from the light source 316 is formed into a ring-shaped light flux by the ring slit 312 and then reflected by the perforated mirror 303 to illuminate the fundus Er of the subject's eye E. The reflected light flux from the fundus Er passes through the perforated mirror 303, and an image of the light is then formed onto the fundus observation CCD 172. Based on the image of the reflected light of the fundus Er that is formed on the fundus observation CCD 172, the CCD control unit 102 generates fundus plane image data and then sends the fundus plane image data to the computer 1003.

Meanwhile, tomographic image data obtained by the OCT optical system contains information about the depth direction but has a problem that it is difficult to identify the position of the cross section in the fundus plane. When a doctor finds a retinal disease from tomographic image data of the retina, if the doctor cannot identify the exact position of the retinal disease in the fundus plane, it is difficult to provide appropriate medical treatment. Thus, the ophthalmic apparatus is configured in such a way that fundus plane image data showing the fundus plane can be acquired. For example, an apparatus including a combination of a fundus camera and an OCT optical system, and an apparatus including a combination of a scanning laser ophthalmoscope (SLO) and an OCT optical system are known. Such ophthalmic apparatuses are configured to display fundus plane image data overlaid with tomographic image data, whereby the position in the fundus plane where the tomographic image data is obtained can be identified. Meanwhile, if the OCT optical system is combined with an optical system for acquiring two-dimensional fundus images, a plurality of imaging light sources and optical systems is required, causing an increase in the price of the apparatus. Thus, pseudo plane image data to be described below may be acquired as a two-dimensional image of the fundus by using the tomographic image data acquired by the OCT optical system, without using the optical system for obtaining two-dimensional fundus images.

Next, the ophthalmic apparatus 100 controls the X-Y scanner 134 to capture fundus tomographic image data showing a cross section of the fundus Er of the subject's eye E. The light emitted from the light source 101 passes through the optical fiber 131-1 and is then divided by the optical coupler 131 into measurement light that is to travel toward the subject's eye E and reference light that is to travel toward the reference mirror 132-4.

The measurement light to travel toward the subject eye's E passes through the optical fiber 131-2, is emitted from the fiber end, and then enters the X-Y scanner 134. The measurement light polarized by the X-Y scanner 134 passes through the optical system 135-1 to illuminate the fundus Er of the subject's eye E. The measurement light is then reflected by the subject's eye E, and the reflected light travels back the path to return to the optical coupler 131.

On the other hand, the reference light to travel toward the reference mirror 132-4 passes through the optical fiber 131-3, is emitted from the fiber end, and then passes through the lens 135-7 and the dispersion compensation glass 115 to reach the reference mirror 132-4. The reference light is reflected by the reference mirror 132-4, and the reflected light travels back the path to return to the optical coupler 131.

The measurement light and the reference light having returned to the optical coupler 131 interfere with each other to form interference light. The interference light enters the optical fiber 131-4, is formed into substantially parallel light by the lens 135-8, and then enters the grating 181. An image of the interference light input to the grating 181 is formed onto the line sensor 182 by the lens 135-9, whereby an interference signal of a single point on the fundus Er of the subject's eye E can be acquired.

The interference signal acquired by the line sensor 182 is output to the computer 1003 to undergo wavenumber conversion processing and Fast Fourier transform (FFT) processing so that the interference signal is visualized as fundus tomographic image data (A-scan information) of the single point on the fundus Er of the subject's eye E in the depth direction.

After the ophthalmic apparatus 100 acquires the fundus tomographic image data of the single point on the fundus Er of the subject's eye E, the ophthalmic apparatus 100 drives the X-Y scanner 134 in the X-direction to generate interference light of another single point on the fundus Er of the subject's eye E. The interference light of that another single point travels via the line sensor 182 and is formed into fundus tomographic image data of that another single point on the fundus Er of the subject's eye E in the depth direction. The driving of the X-Y scanner 134 in the X-direction is repeated, whereby a single set of fundus tomographic image data (B-scan information) of the fundus Er of the subject's eye E in the horizontal direction can be generated.

Then, after the XY scanner 134 is driven for a predetermined amount in the Y-direction, the scanning in the X-direction described above is performed again, whereby fundus tomographic image data of another position on the fundus Er of the subject's eye E in the Y-direction can be generated. The driving of the XY scanner 134 in the Y-direction is repeated to generate a plurality of sets of fundus tomographic image data covering a predetermined range of the fundus Er. The optical head 1000 is an example of the ophthalmic imaging apparatus, and the computer 1003 is an example of the image processing apparatus.

(Method of Generating Intensity Image Data)

Figure 2:
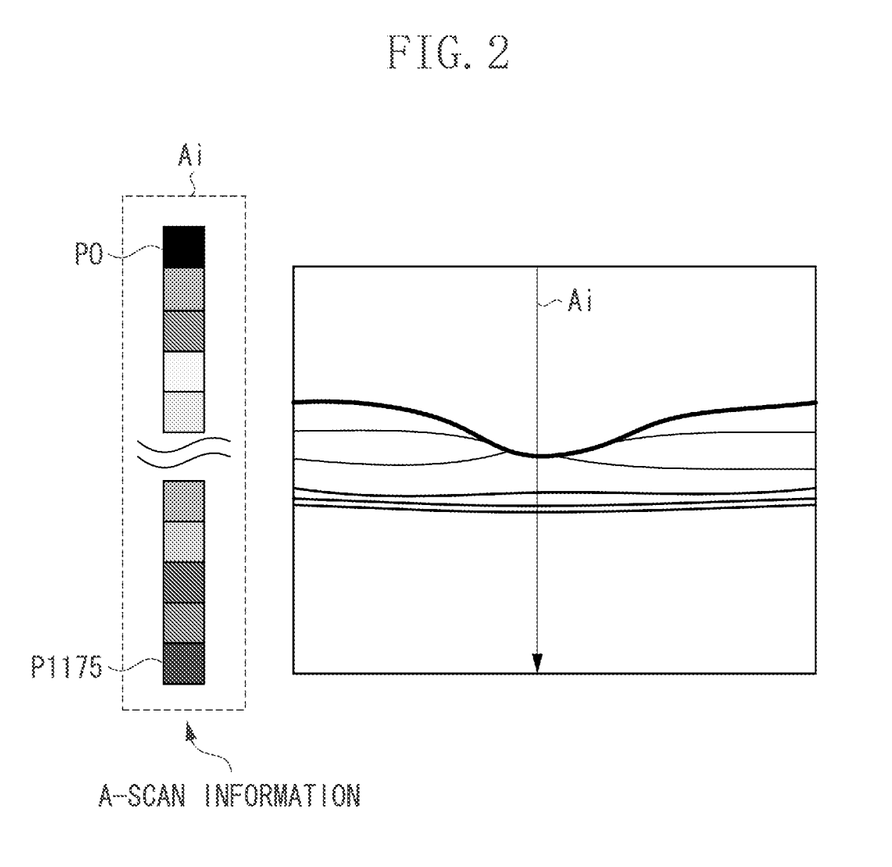
FIG. 2 illustrates a method of generating intensity image data.

The following describes processing of generating pseudo plane image data (intensity image data) of the retina from the plurality of sets of fundus tomographic image data thus generated. As described above, the A-scan information is fundus tomographic image data of a single point (Ai) on the fundus Er of the subject's eye E in the depth direction and, as illustrated in FIG. 2, contains a plurality of pieces of luminance information in the depth direction. For example, the ophthalmic apparatus 100 employs the line sensor 182 having 2048 pixels, and the A-scan information Ai having undergone the FFT includes 1176 pieces of luminance information. In FIG. 2, P0 denotes luminance information regarding the shallowest portion in the depth direction, and P1175 denotes luminance information regarding the deepest portion in the depth direction.

A conventional optical coherence tomographic imaging apparatus acquires intensity information about a single point on the fundus Er of the subject's eye E by adding and averaging all or some of the pieces of luminance information included in the A-scan information Ai. Conventionally, the direction of the A-scan information Ai is the same as the direction of the measurement light and is always perpendicular with respect to the depth direction of the fundus tomographic image data. The intensity information is determined for every piece of A-scan information, whereby the intensity information on each different point on the fundus E can be acquired. These pieces of intensity information are reconstructed into two-dimensional image data, whereby intensity image data, which is the intensity information regarding the entire retina, can be acquired.

Meanwhile, the conventional processing for generating intensity image data acquires intensity information by combining the pieces of luminance information together along the direction of the A-scan information Ai. This processing, however, sometimes cannot provide optimum intensity information. This will be described below, with reference to FIGS. 3 and 4.

(Intensity Image Data in a Case where the Retina is Horizontal)

Figure 3:
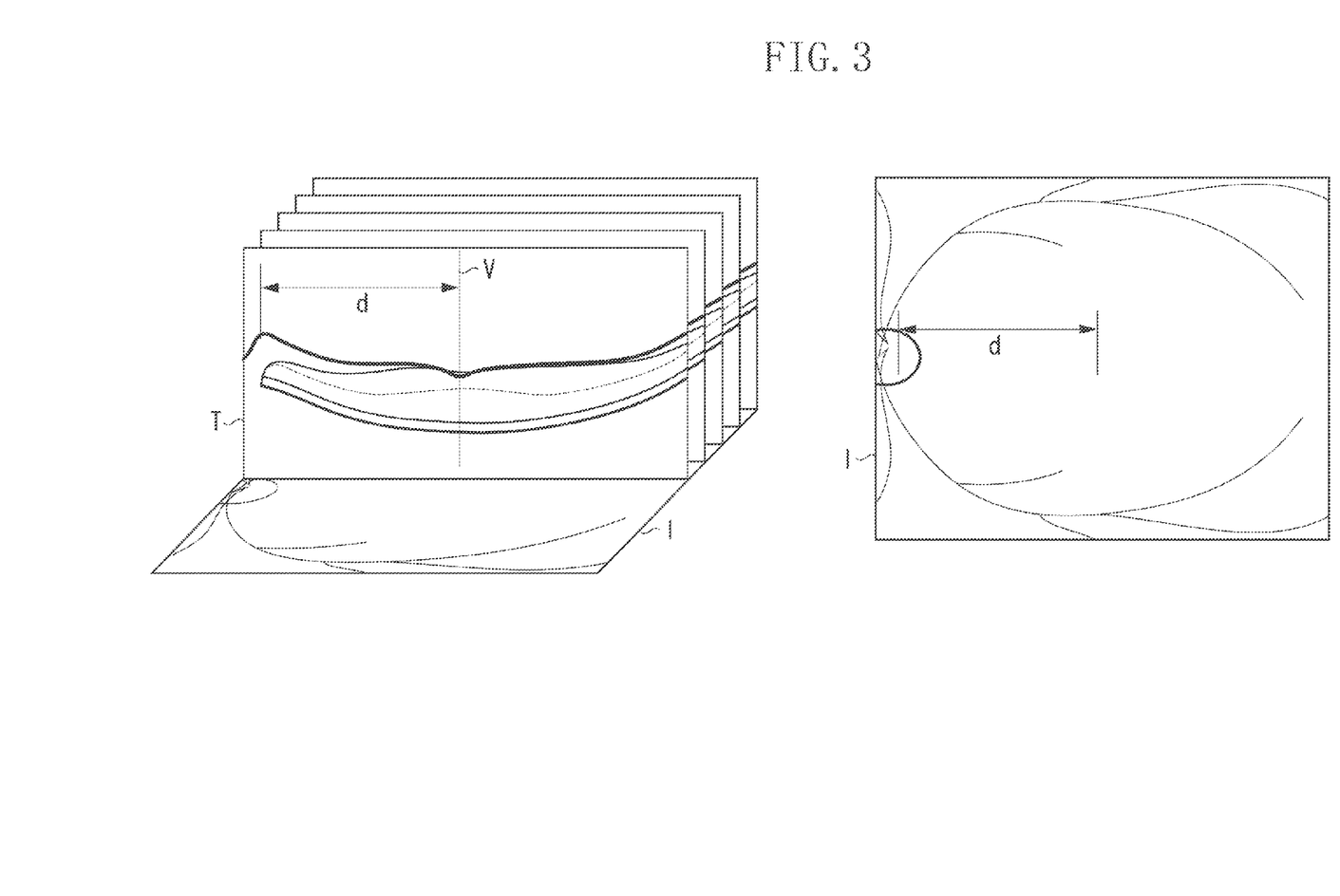
FIG. 3 illustrates an example of intensity image data generated in a case where the retina is horizontally formed on fundus tomographic image data.

FIG. 3 illustrates an example of intensity image data generated in a case where the retina is formed horizontally in the fundus tomographic image data (in a case where there is almost no retinal tilt in the fundus tomographic image data). If the state of the subject's eye E is stable and the effect of cataract or opacity of the subject's eye E is small, imaging can be performed in such a way that the retina is substantially horizontal in fundus tomographic image data T. Then, pieces of luminance information of the fundus tomographic image data T are combined together along a depth direction V of the fundus tomographic image data T, which is the same direction as the direction of the A-scan information, to generate intensity image data I. The acquired intensity image data I is high-quality image data with less distortion and is suitable for use in measurement of a distance or size. For example, a distance d from a rim of the optic disc to the center of macula that is designated in the fundus tomographic image data T is also shown as a distance d in the intensity image data I and can be used as efficient information for diagnosis.

(Intensity Image Data in a Case where the Retina is Tilted from the Horizontal Direction)

Figure 4:
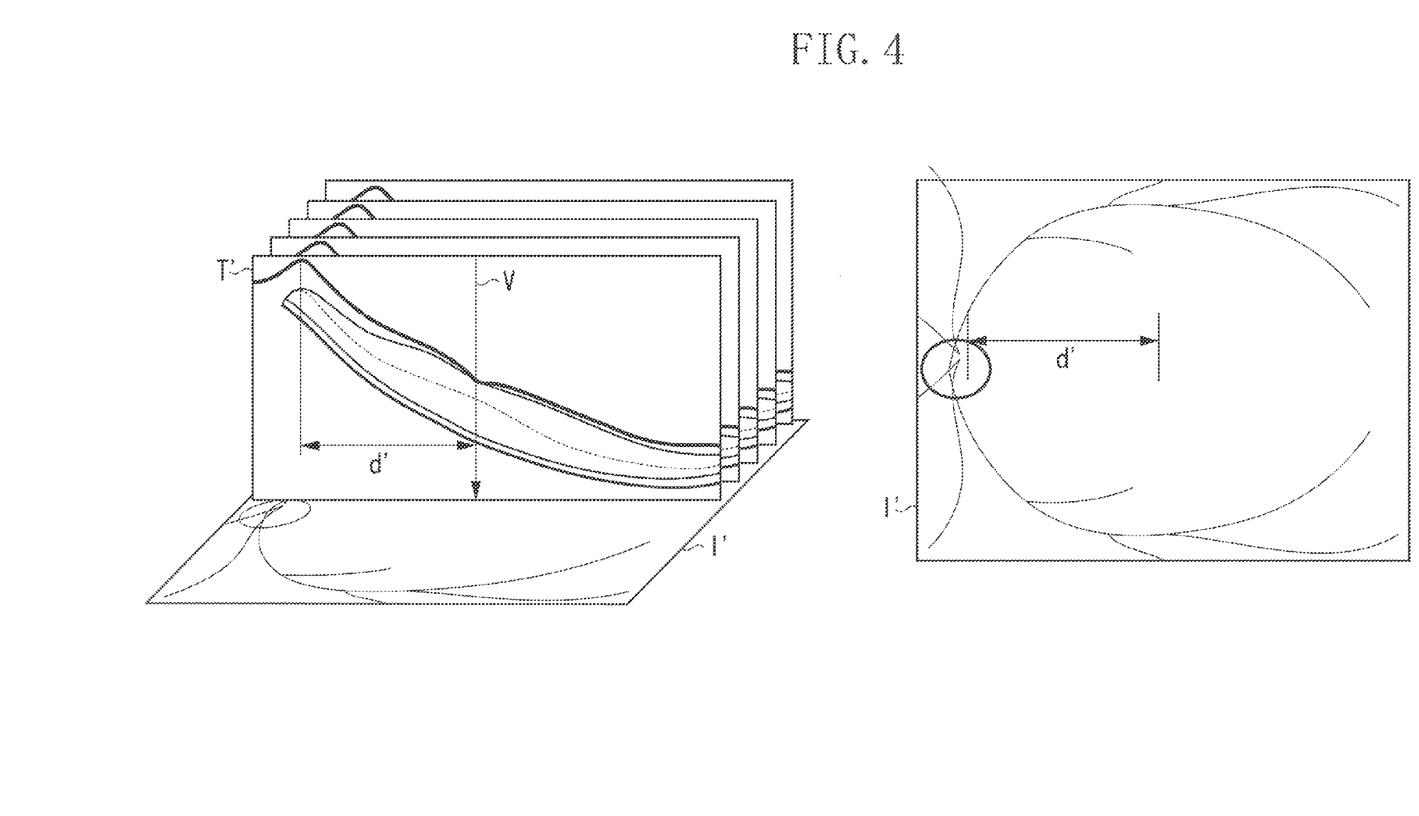
FIG. 4 illustrates an example of intensity image data generated in a case where the retina is formed on fundus tomographic image data in such a way that the retina is tilted with respect to the horizontal direction of the fundus tomographic image data.

FIG. 4 illustrates an example of a captured image of the subject eye E illustrated in FIG. 3, showing an example of intensity image data that is generated in a case where the retina is formed in such a way that the retina is tilted with respect to the horizontal direction of fundus tomographic image data T'. For example, if contract or opacity is observed in the subject's eye E, an operator adjusts the position of the optical head 1000 in such a way that the measurement light enters the retina while avoiding the opacity. Thus, the measurement light enters the subject's eye E from an offset position, and, as a result, the retina is formed in such a way that the retina is tilted with respect to the horizontal direction of the fundus tomographic image data T'. Such a tilted retina is observed when the position of the subject's eye E is unstable or the subject's eye E itself is tilted.

Accordingly, when the retina is tilted with respect to the horizontal direction of the fundus tomographic image data T', if the pieces of luminance information of the fundus tomographic image data T' are combined together in the depth direction V of the fundus tomographic image data T', which is the same direction as the direction of the A-scan information, the pieces of luminance information are combined together in an oblique direction with respect to the retina. The resulting intensity image data I' is unclear image data different from the original intensity image data I.

Further, when the retina is tilted with respect to the horizontal direction of the fundus tomographic image data T', the range of the retina formed in the fundus tomographic image data T' changes, so the generated intensity image data I' is also distorted. For example, the distance d' from the rim of the optic disc to the center of macula that is designated in the fundus tomographic image data T' is measured as a distance that is clearly different from the distance d in FIG. 3, which illustrates the same subject's eye E from the front.

This variation in measured values can cause a problem when the size of a lesion portion is compared among a plurality of examinations.

(Method of Generating Intensity Image Data According to the First Exemplary Embodiment)

Figure 5:
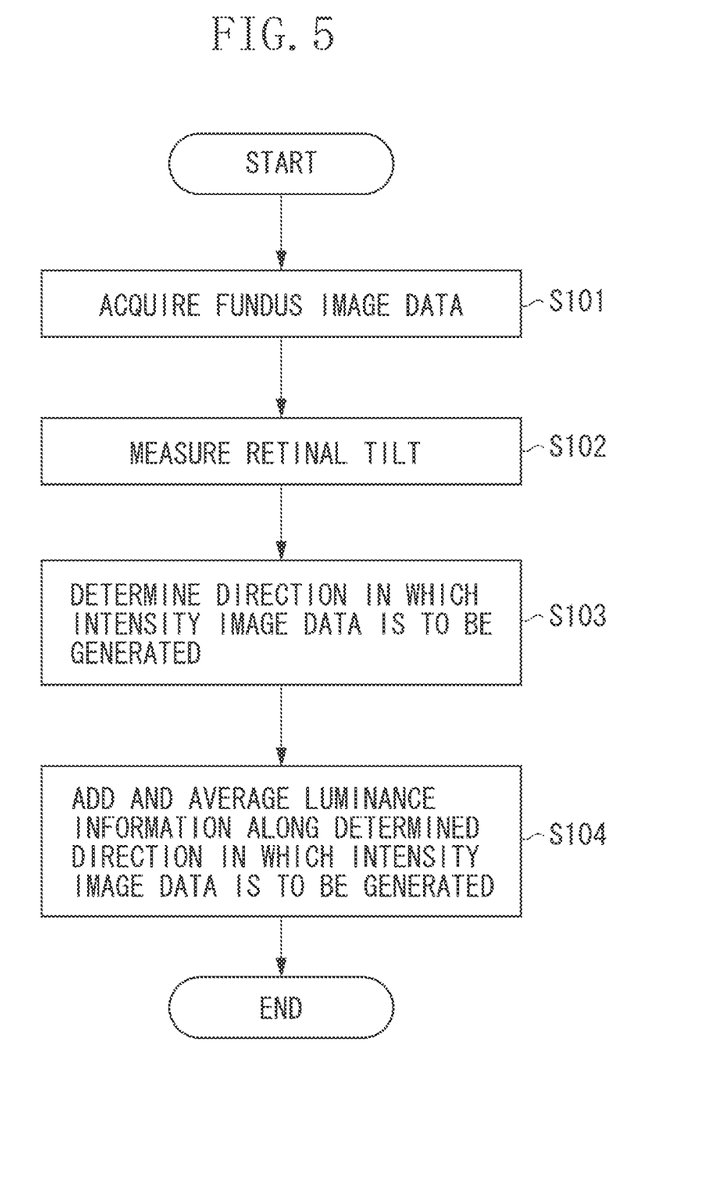
FIG. 5 is a flowchart illustrating processing executed by a computer according to a first exemplary embodiment of the present invention.

In the present exemplary embodiment, the pieces of luminance information of the fundus tomographic image data are combined together in the direction that is substantially perpendicular to the retina to generate intensity image data. The following describes a method thereof, with reference to FIGS. 5 to 7. FIG. 5 is a flowchart illustrating processing executed by the computer 1003. A central processing unit (CPU) in the computer 1003 reads a necessary program and data stored in a storage medium such as a read-only memory (ROM) and hard disk drive (HDD) and executes the program to implement the processing illustrated in FIG. 5.

Figure 6A:
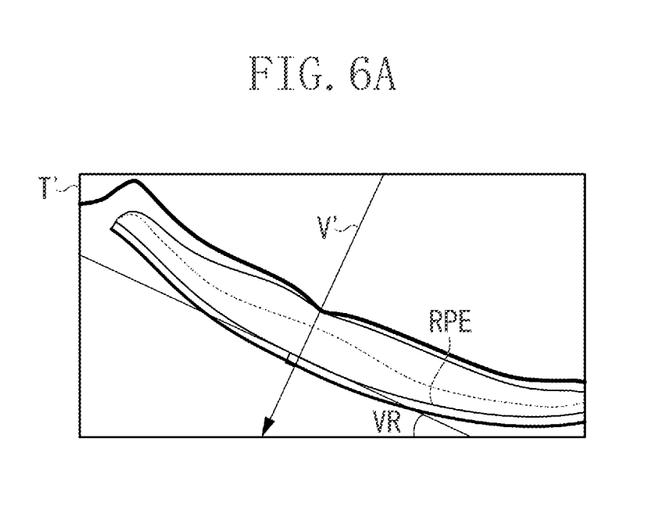
FIGS. 6A and 6B each illustrate a direction in which pieces of luminance information of fundus tomographic image data are combined together according to the first exemplary embodiment of the present invention.

In step S101, the computer 1003 acquires fundus image data captured by the optical head 1000. In step S102, the computer 1003 measures information (hereinafter, referred to simply as "retinal tilt") VR indicating the retinal tilt with respect to the horizontal direction of the fundus tomographic image data, as illustrated in FIG. 6A. The retina has a multilayer structure, and the retinal tilt VR is desirably measured using at least one of the layer shapes and layer boundaries. In the present exemplary embodiment, the retinal tilt VR is measured based on the shape of the retinal pigment epithelium (RPE) at the central fovea and the shape of the Bruch's membrane (BM) existing at the base of the RPE.

In the case of a normal eye, the Bruch's membrane and the retinal pigment epithelium have the same shape, so either one can be used to determine the retinal tilt VR. However, when a disease such as age-related macular degeneration is observed, the retinal pigment epithelium and other retinal layers are deformed from their original shapes in many cases. Thus, if a retinal disease exists, it is desirable to determine the retinal tilt VR by use of the Bruch's membrane. In step S103, the computer 1003 determines the direction perpendicular to the retina as the direction V' in which intensity image data is to be generated, based on the determined retinal tilt VR.

Figure 6B:
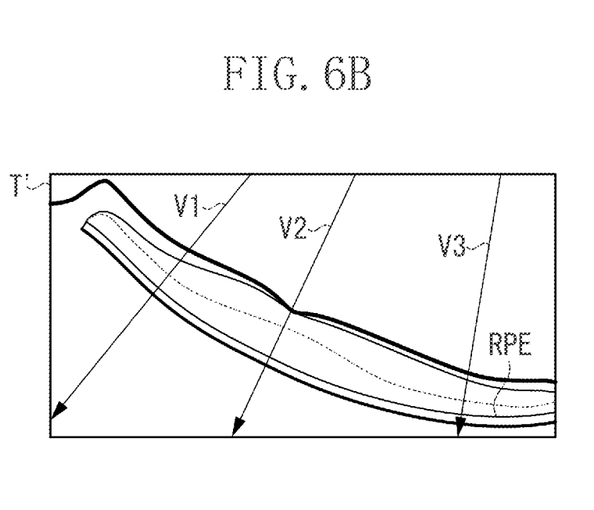

The directions V1 to V3 in which intensity image data is to be generated can be determined at a site other than the central fovea, as illustrated in FIG. 6B. For example, the ophthalmic apparatus 100 acquires the retinal tilt VR at each site of the retina, and based on the retinal tilts VR at the respective sites of the retina, the ophthalmic apparatus 100 determines the directions that are respectively substantially perpendicular to the sites of the retina as the directions V1 to V3 in which the intensity image data is to be generated. The information VR indicating the tilt may also be determined based on the positional relationship between predetermined layers in the tomographic image data in the depth direction. Specifically, the information VR may be determined based on a difference between z-coordinates of ends of a high-luminance layer in the tomographic image data (the coordinates in the depth direction).

Figure 7:
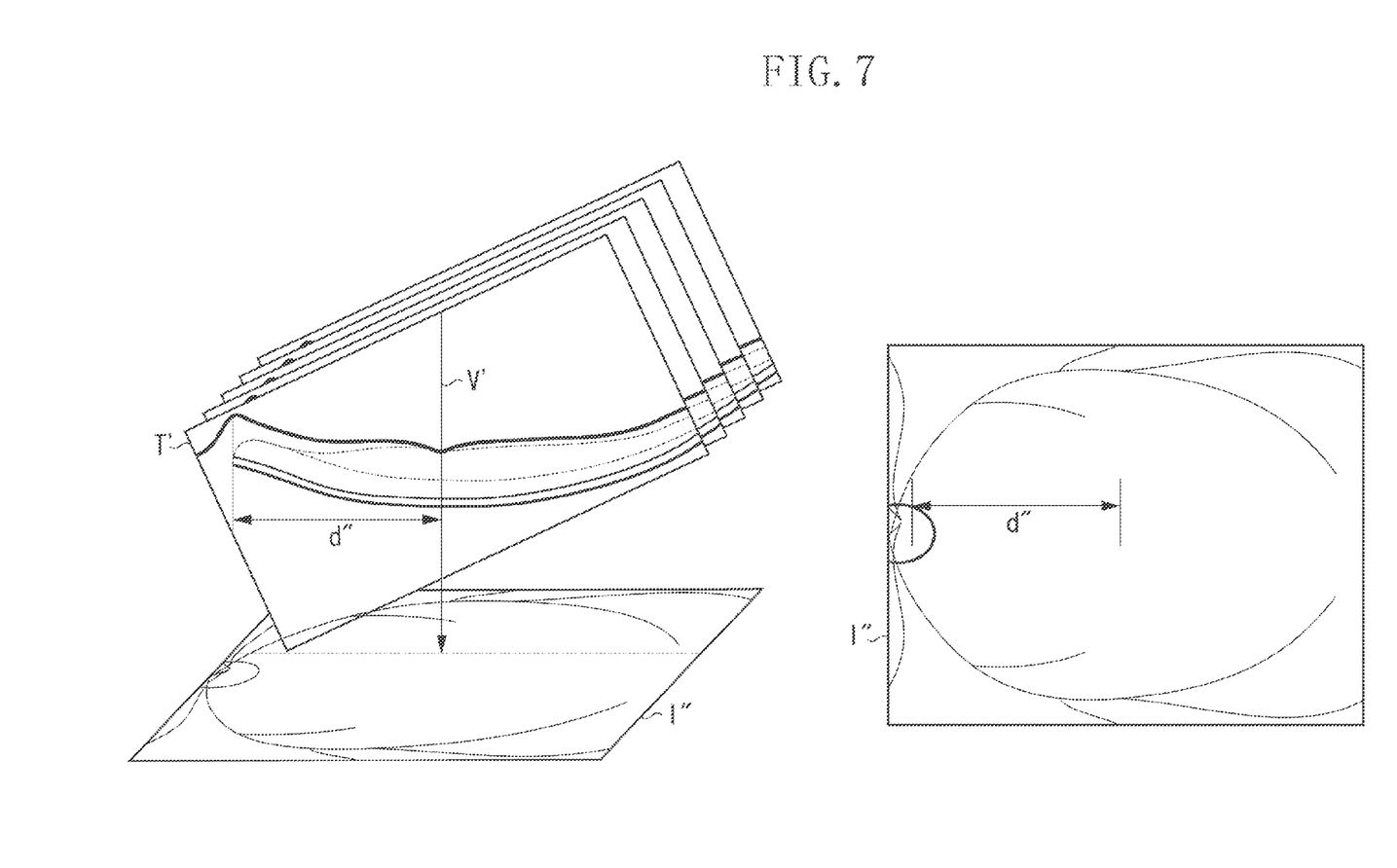
FIG. 7 illustrates a method of generating intensity image data according to the first exemplary embodiment of the present invention.

In step S104, as illustrated in FIG. 7, the computer 1003 adds and averages the pieces of luminance information of the fundus tomographic image data T' along the determined direction V' (or V1 to V3) in which intensity image data is to be generated, thereby generating intensity image data I". The acquired intensity image data I" has substantially the same appearance as that of the appropriate intensity image data I illustrated in FIG. 3. The intensity image data I" has only small distortion. Thus, for example, a distance d" from the rim of the optic disc to the center of macula in the fundus tomographic image data T' is measured as a distance that is substantially equal to the distance d in FIG. 3. Accordingly, appropriate intensity image data can be generated regardless of the retinal tilt in the fundus tomographic image data T'.

(Projection of Area of Fundus Tomographic Image Data onto Intensity Image Data)

The ophthalmic apparatus 100 can also display the intensity image data overlaid with an area set in the fundus tomographic image data. The following describes a method thereof, with reference to FIG. 8.

Figure 8:
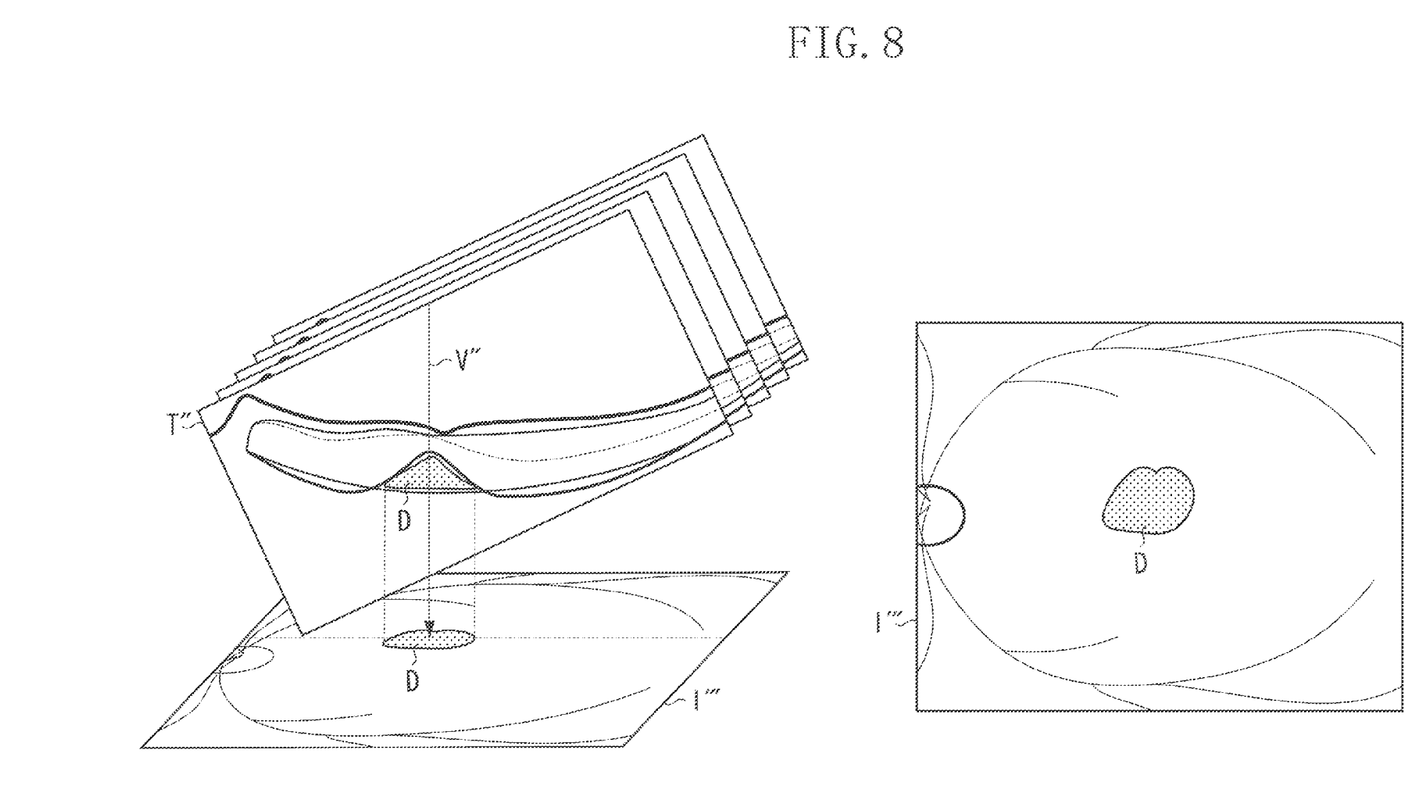
FIG. 8 illustrates a method of projecting an area in fundus tomographic image data onto intensity image data.

First, the ophthalmic apparatus 100 analyzes the fundus tomographic image data T'' to identify a lesion area D. FIG. 8 illustrates an example in which neovascularity is developed beneath the retinal pigment epithelium. The ophthalmic apparatus 100 determines the lesion area D affected by the neovascularity. The lesion area D is not limited to the neovascularity, and any other lesion such as drusen and edema can be determined as the lesion area D, or a structure or area other than a lesion can be set as the lesion area D. Further, an operator can manually designate an area to set the area as the lesion area D.

Next, the ophthalmic apparatus 100 projects the set lesion area D onto intensity image data I''' along a direction V'' that is substantially perpendicular to the tilt of the Bruch's membrane in such a way that the intensity image data I''' is overlaid with the lesion area D, and the ophthalmic apparatus 100 displays it on the monitor 1005. Since the intensity image data I''' only has small distortion associated with the retinal tilt, a doctor can correctly recognize the shape and size of the lesion by observing the intensity image data I'' overlaid with the lesion are D and use them in his/her diagnosis.

While the present exemplary embodiment generates the intensity image data of the retina based on the fundus tomographic image data of the fundus Er of the subject's eye E, the intensity image data of the anterior eye portion can be generated based on anterior eye tomographic image data showing a cross section of the anterior eye portion of the subject's eye E. In this case, the tilt of the anterior eye portion in the anterior eye tomographic image data can be measured based on the cornea or crystalline lens formed in the anterior eye tomographic image data, and a direction that is substantially perpendicular to the anterior eye portion can be determined as the direction in which intensity image data is to be generated (direction in which pieces of luminance information are to be combined together).

The following describes the second exemplary embodiment of the present invention. The configuration of an ophthalmic apparatus according to the second exemplary embodiment is similar to that of the ophthalmic apparatus according to the first exemplary embodiment illustrated in FIG. 1, and thus the same reference numerals used in FIG. 1 will be used in the following description. Further, an imaging method of the ophthalmic apparatus according to the second exemplary embodiment is similar to that of the first exemplary embodiment, except for the method of generating intensity image data.

Figure 9:
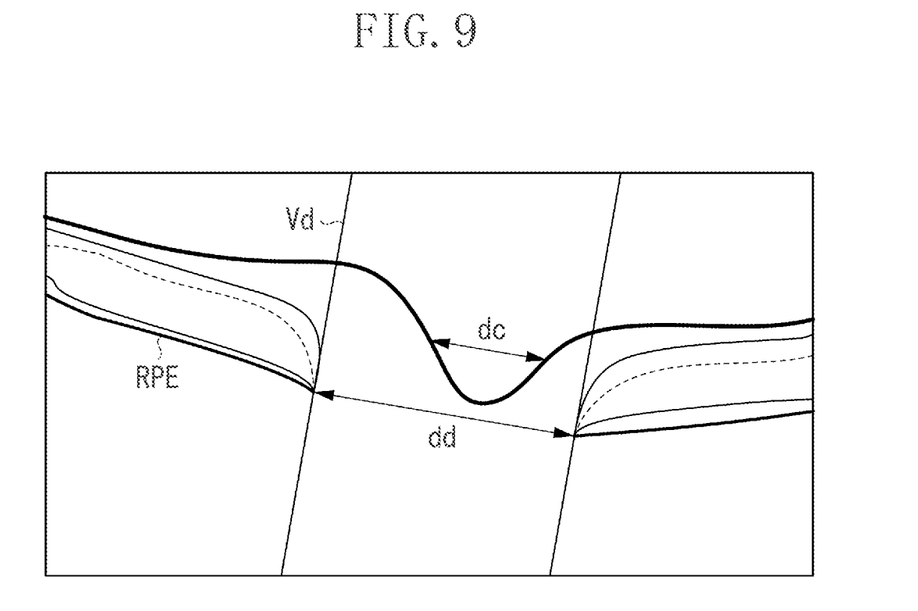
FIG. 9 illustrates a method of generating intensity image data according to a second exemplary embodiment of the present invention.

In the second exemplary embodiment, the direction in which intensity image data is to be generated is determined based on the shape of the optic disc (Disc). FIG. 9 illustrates fundus tomographic image data showing the retina around the optic disc that is captured by the ophthalmic apparatus 100. The RPE is known to disappear at the site of the optic disc (Disc), and two end points of the RPE appear within the fundus tomographic image data. The ophthalmic apparatus 100 detects the two RPE end points in each fundus tomographic image data and connects the RPE end points together so that the shape and size dd of the optic disc (Disc) can be measured. Furthermore, the shape and size dc of the optic disc cupping (Cup) can be measured from the shape of the optic disc.

Next, the ophthalmic apparatus 100 determines a direction Vd in which intensity image data is to be generated in a direction that is substantially perpendicular with respect to a straight line connecting the detected two RPE end points. Then, the ophthalmic apparatus 100 adds and averages the pieces of luminance information of the fundus tomographic image data along the direction Vd, thereby generating intensity image data.

Figure 10:
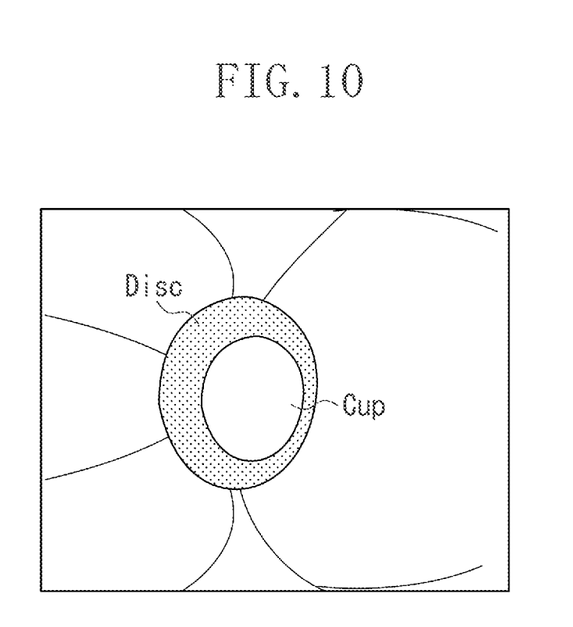
FIG. 10 illustrates an example in which the shapes of optic disc and optic disc cupping are projected on intensity image data.

Further, as illustrated in FIG. 10, the ophthalmic apparatus 100 projects the shapes of the detected optic disc (Disc) and the detected optic disc cupping (Cup) onto the intensity image data in such a way that the intensity image data is overlaid with the shapes along the direction Vd, and the ophthalmic apparatus 100 displays it on the monitor 1005. This enables a doctor to observe the shape and size of the optic disc in the intensity image data of the optic disc portion with small distortion.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-164230 filed Aug. 7, 2013, which is hereby incorporated by reference herein in its entirety.

What is claimed is:

1. An image processing apparatus comprising:
   an acquisition unit configured to acquire luminance information of a three-dimensional tomographic image of an object;
   a measurement unit configured to measure information indicating a tilt of the object in the three-dimensional tomographic image;
   a determination unit configured to determine a direction based on the measured information; and
   a generation unit configured to generate a plane image of the object by combining the acquired luminance information along the determined direction.

2. The image processing apparatus according to claim 1, wherein, based on the measured information indicating the tilt of the object, the determination unit determines a direction that is substantially perpendicular to the object as the direction in which the luminance information of the three-dimensional tomographic image is to be combined.

3. The image processing apparatus according to claim 2, wherein the determination unit determines a plurality of substantially perpendicular directions respectively corresponding to a plurality of predetermined sites of the object as the direction in which the luminance information of the three-dimensional tomographic image is to be combined.

4. The image processing apparatus according to claim 1, further comprising a projection unit configured to project a specific area in the three-dimensional tomographic image onto the plane image along the determined direction.

5. The image processing apparatus according to claim 4, further comprising an area determination unit configured to determine the specific area based on the three-dimensional tomographic image.

6. The image processing apparatus according to claim 5, wherein the object is a subject's eye, and
   wherein the area determination unit determines, based on a retinal pigment epithelium of a fundus of the subject's eye formed on the three-dimensional tomographic image, an optic disc of the fundus as the specific area.

7. The image processing apparatus according to claim 6, wherein the area determination unit further determines optic disc cupping as the specific area based on the optic disc.

8. The image processing apparatus according to claim 1, wherein the object is a subject's eye, and
   wherein the measurement unit measures, based on a Bruch's membrane or retinal pigment epithelium of a fundus of the subject's eye formed on the three-dimensional tomographic image, information indicating a tilt of the fundus in the three-dimensional tomographic image.

9. The image processing apparatus according to claim 1, wherein the object is a subject's eye, and
   wherein the image processing apparatus further comprises a measurement unit configured to measure, based on a cornea or crystalline lens of an anterior eye portion of the subject's eye formed on the three-dimensional tomographic image, information indicating a tilt of the anterior eye portion in the three-dimensional tomographic image.

10. An image processing system in which the image processing apparatus according to claim 1 and an ophthalmic imaging apparatus are communicably connected to each other, wherein the acquisition unit of the image processing apparatus acquires the three-dimensional tomographic image of the object captured by the ophthalmic imaging apparatus.

11. An image processing method executed by an image processing apparatus, the image processing method comprising:
    acquiring luminance information of a three-dimensional tomographic image of an object;
    measuring information indicating a tilt of the object in the three-dimensional tomographic image;
    determining a direction based on the measured information; and
    generating a plane image of the object by combining the acquired luminance information along the determined direction.

12. The image processing method according to claim 11, wherein, a direction that is substantially perpendicular to the object is determined, based on the measured information indicating the tilt of the object, as the direction in which the luminance information of the three-dimensional tomographic image is to be combined.

13. The image processing method according to claim 12, wherein a plurality of substantially perpendicular directions respectively corresponding to a plurality of predetermined sites of the object is determined as the direction in which the luminance information of the three-dimensional tomographic image is to be combined.

14. The image processing method according to claim 11, further comprising projecting a specific area in the three-dimensional tomographic image onto the plane image along the determined direction.

15. The image processing method according to claim 14, further comprising determining the specific area based on the three-dimensional tomographic image.

16. The image processing method according to claim 15, wherein the object is a subject's eye, and
wherein an optic disc of the fundus is determined, based on a retinal pigment epithelium of a fundus of the subject's eye formed on the three-dimensional tomographic image, as the specific area.

17. The image processing method according to claim 16, wherein optic disc cupping is determined as the specific area based on the optic disc.

18. The image processing method according to claim 11, wherein the object is a subject's eye, and
wherein information indicating a tilt of the fundus in the three-dimensional tomographic image is determined based on a Bruch's membrane or retinal pigment epithelium of a fundus of the subject's eye formed on the three-dimensional tomographic image.

19. The image processing method according to claim 11, wherein the object is a subject's eye, and
wherein information indicating a tilt of the anterior eye portion in the three-dimensional tomographic image is determined based on a cornea or crystalline lens of an anterior eye portion of the subject's eye formed on the three-dimensional tomographic image.

20. A non-transitory computer-readable storage medium storing a program for causing a computer to execute the image processing method according to claim 11.

21. An image processing apparatus comprising:
an acquisition unit configured to acquire luminance information of at least a portion of a three-dimensional tomographic image of an object;
a measurement unit configured to measure information indicating a tilt of the object in the three-dimensional tomographic image;
a determination unit configured to determine a direction based on the measured information; and
a generation unit configured to generate a plane image of the object based on the determined direction and the acquired luminance information.

22. The image processing apparatus according to claim 21,
wherein the determination unit determines each pixel value in the plane image based on the determined direction and the acquired luminance information, and
wherein the generation unit generates the plane image based on the determined each pixel value.

23. The image processing apparatus according to claim 22, wherein the determination unit determines the each pixel value by combining the acquired luminance information along the determined direction.

24. The image processing apparatus according to claim 22, wherein the determination unit determines the each pixel value by assigning a pixel value per pixel from the acquired luminance information along the determined direction.

25. An image processing method comprising:
acquiring luminance information of at least a portion of a three-dimensional tomographic image of an object;
measuring information indicating a tilt of the object in the three-dimensional tomographic image;
determining a direction based on the measured information; and
generating a plane image of the object based on the determined direction and the acquired luminance information.

26. The image processing method according to claim 25, wherein each pixel value in the plane image is determined based on the determined direction and the acquired luminance information, and
wherein the plane image is generated based on the determined each pixel value.

27. The image processing method according to claim 26, wherein the each pixel value is determined by combining the acquired luminance information along the determined direction.

28. The image processing method according to claim 26, wherein the each pixel value is determined by assigning a pixel value per pixel from the acquired luminance information along the determined direction.

29. A non-transitory computer-readable storage medium storing a program for causing a computer to execute the image processing method according to claim 25.

* * * * *